(12) United States Patent
Thomas et al.

(10) Patent No.: US 11,364,338 B2
(45) Date of Patent: Jun. 21, 2022

(54) INFUSION DEVICE HAVING A CLUTCHING DEVICE

(71) Applicant: Fresenius Vial SAS, Brézins (FR)

(72) Inventors: Fabien Thomas, Saint Victor de Cessieu (FR); Damien Archat, Grénoble (FR); Denis Bertagnolio, Sillans (FR)

(73) Assignee: Fresenius Vial SAS, Brézins (FR)

( * ) Notice: Subject to any disclaimer, the term of this patent is extended or adjusted under 35 U.S.C. 154(b) by 541 days.

(21) Appl. No.: 16/329,041

(22) PCT Filed: Aug. 25, 2017

(86) PCT No.: PCT/EP2017/071399
§ 371 (c)(1),
(2) Date: Feb. 27, 2019

(87) PCT Pub. No.: WO2018/046313
PCT Pub. Date: Mar. 15, 2018

(65) Prior Publication Data
US 2019/0224408 A1  Jul. 25, 2019

(30) Foreign Application Priority Data
Sep. 7, 2016 (EP) .................................... 16306118

(51) Int. Cl.
*A61M 5/14* (2006.01)
*A61M 5/145* (2006.01)
*A61M 5/142* (2006.01)

(52) U.S. Cl.
CPC .......... *A61M 5/1458* (2013.01); *A61M 5/142* (2013.01); *A61M 5/1452* (2013.01);
(Continued)

(58) Field of Classification Search
CPC ...... A61M 5/1452; A61M 2005/14533; A61M 5/1456; A61M 5/1458
See application file for complete search history.

(56) References Cited

U.S. PATENT DOCUMENTS

| 4,424,720 A | 1/1984 | Bucchianeri |
| 5,176,646 A * | 1/1993 | Kuroda ............... A61M 5/1456 128/DIG. 1 |

(Continued)

FOREIGN PATENT DOCUMENTS

| CN | 102325558 | 1/2012 |
| CN | 103920211 | 7/2014 |

(Continued)

OTHER PUBLICATIONS

International Search Report and Written Opinion, counterpart International Appl. No. PCT/EP2017/071399 (dated Oct. 18, 2017) (13 pages).

(Continued)

*Primary Examiner* — William R Carpenter
(74) *Attorney, Agent, or Firm* — Cook Alex Ltd.

(57) ABSTRACT

All infusion device (1) for administering a medical fluid to a patient comprises a receptacle (11) for receiving a syringe (2), a pusher device (12) movable in a pushing direction (P) for acting onto a piston (21) of the syringe (2) received in the receptacle (11), a driving rod (14), an electric drive device (141) for driving the driving rod (14), and a clutching device (13) comprising a frame member (131) and at least one clutch element (130A, 130B) movably arranged on the frame member (131). The at least one clutch element (130A, 130B) is constituted to operatively connect, in a clutched state, the driving rod (14) to the pusher device (12) for driving the pusher device (12) by the electric drive device (141). The clutching device (13) is actuatable to assume an unclutched state in which the operative connection between (Continued)

the driving rod (14) and the pusher device (12) is released. Herein the clutching device (13) comprises a lock element (19) for locking the at least one clutch element (130A, 130B) in the clutched state. In this way, an infusion device is provided which in an easy and reliable manner allows for maintaining the clutching device in the clutched state during operation of the infusion device.

10 Claims, 7 Drawing Sheets

(52) U.S. Cl.
CPC . *A61M 5/1456* (2013.01); *A61M 2005/14208* (2013.01); *A61M 2205/33* (2013.01); *A61M 2205/50* (2013.01)

(56) References Cited

U.S. PATENT DOCUMENTS

| | | | |
|---|---|---|---|
| 6,387,077 B1* | 5/2002 | Klibanov | A61M 5/1456 128/DIG. 1 |
| 6,423,035 B1 | 7/2002 | Das et al. | |
| 2002/0077598 A1 | 6/2002 | Yap et al. | |
| 2007/0074596 A1 | 4/2007 | Siefert | |
| 2012/0088206 A1* | 4/2012 | Tanaka | A61M 5/20 433/90 |
| 2012/0215170 A1* | 8/2012 | Traversaz | A61M 5/14546 604/155 |
| 2014/0088553 A1 | 3/2014 | Hetherington | |
| 2014/0343533 A1 | 11/2014 | Gerlach et al. | |
| 2015/0094665 A1 | 4/2015 | Heitmeier et al. | |
| 2015/0157791 A1 | 6/2015 | Desch et al. | |
| 2016/0235908 A1 | 8/2016 | Schmid | |
| 2017/0258985 A1* | 9/2017 | Adams | A61B 50/00 |

FOREIGN PATENT DOCUMENTS

| | | |
|---|---|---|
| CN | 104147657 | 11/2014 |
| EP | 0916353 | 5/1999 |
| EP | 1110569 | 7/2006 |
| EP | 2554197 | 2/2013 |
| EP | 2599511 | 8/2014 |
| GB | 2480407 | 11/2011 |
| JP | 2002-191693 | 7/2002 |
| WO | WO 02/092153 A2 | 11/2002 |
| WO | WO2013/092889 | 6/2013 |
| WO | WO 2014/107630 A2 | 7/2014 |

OTHER PUBLICATIONS

Search Report, corresponding Chinese application No. 201780054116.5 (dated Dec. 11, 2020) (2 pages).
Office Action, corresponding Chinese application No. 201780054116.5 (dated Dec. 22, 2020) (12 pages).
Response to Notice of Opposition with auxiliary requests, counterpart EP application No. 17758508 (Aug. 25, 2021) (43 pages).
Notice of Opposition with English-language machine-translation, counterpart EP application No. 17758508 (Mar. 9, 2021) (66 pages).
Response to opponent's letter dated Nov. 18, 2021, counterpart EP application No. 17758508 (Dec. 16, 2021) (13 pages).
Opponent's letter with English-language machine-translation, counterpart EP application No. 17758508 (Nov. 18, 2021) (14 pages).

\* cited by examiner

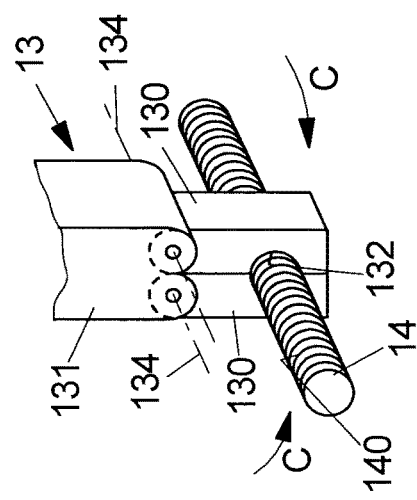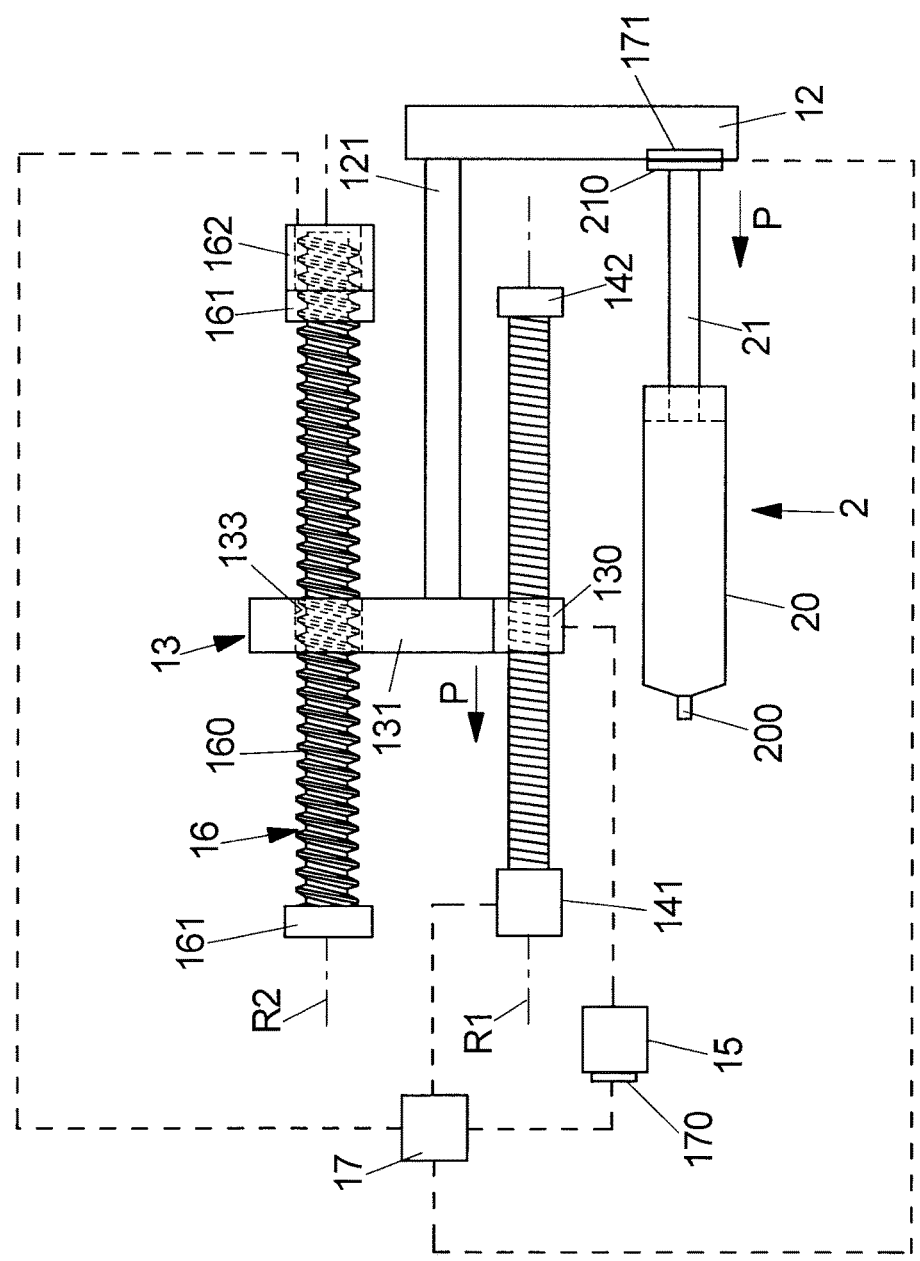

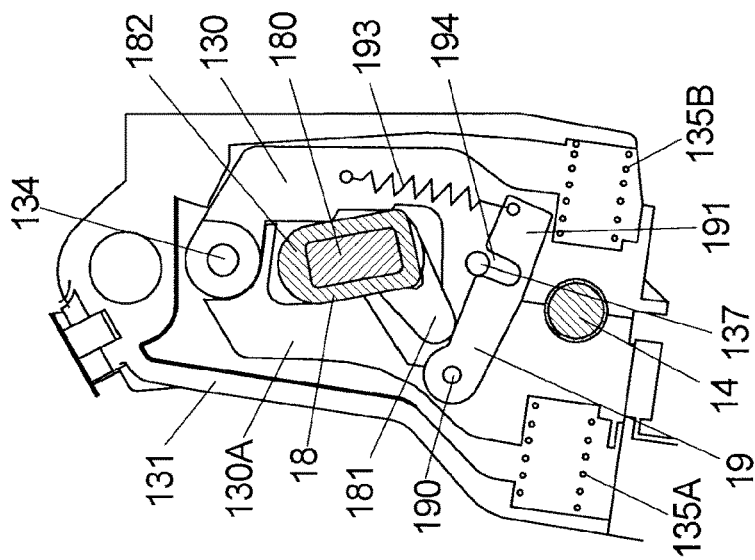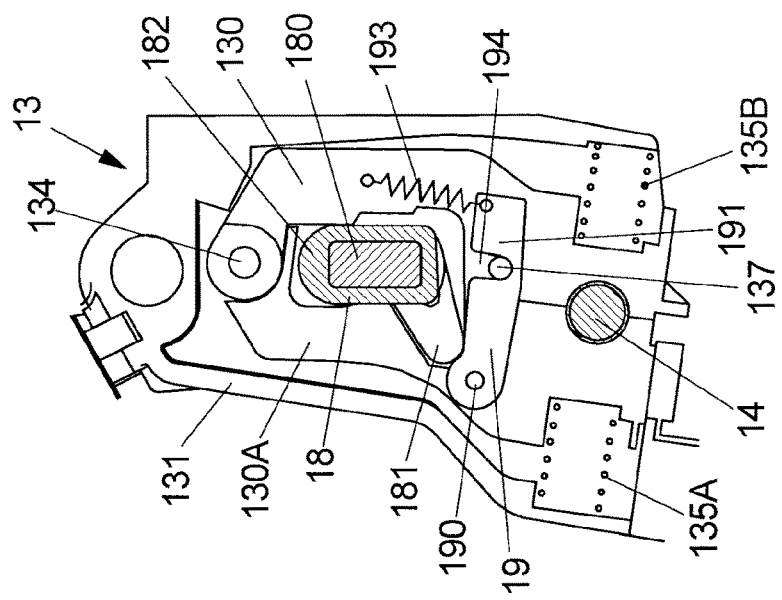

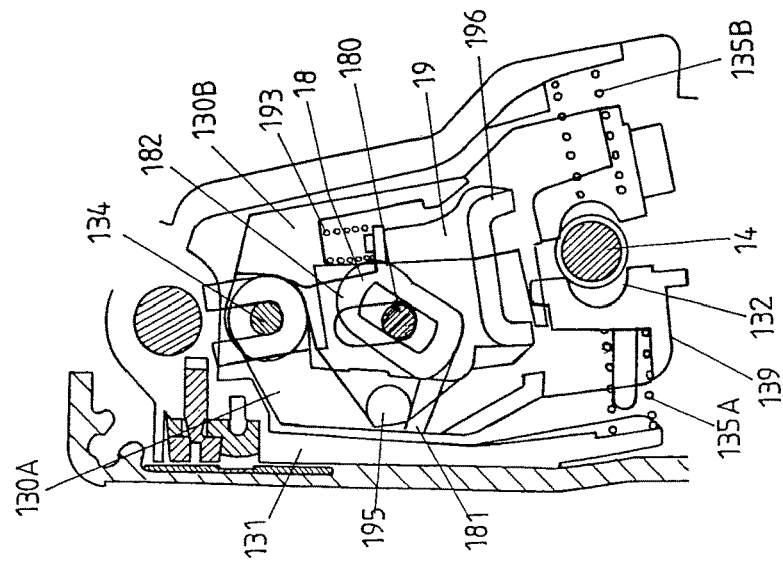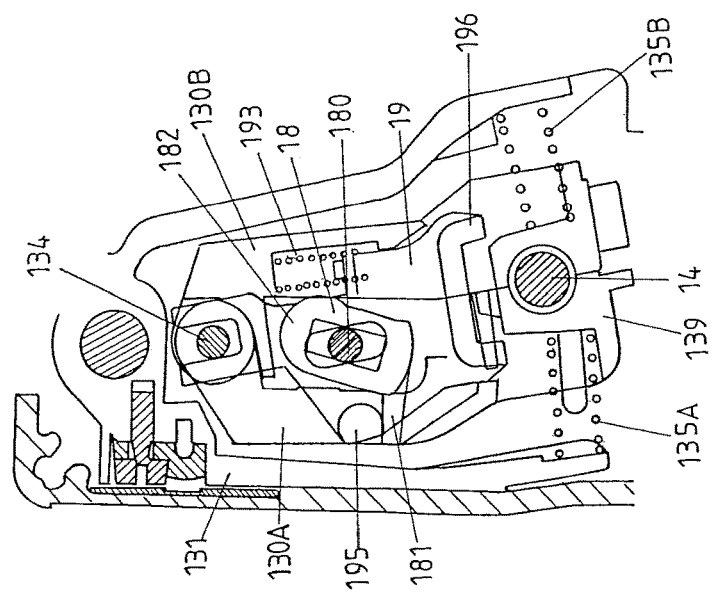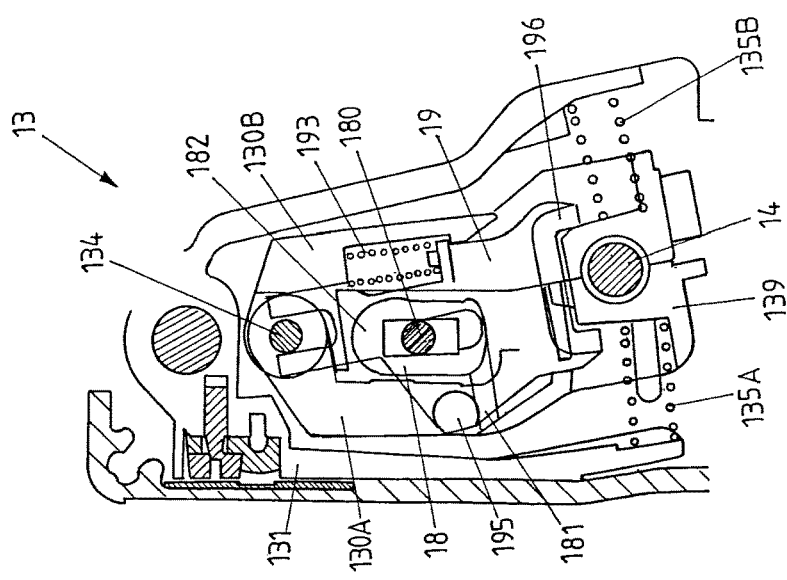

INFUSION DEVICE HAVING A CLUTCHING DEVICE

The present application is a U.S. National Stage of PCT International Patent Application No. PCT/EP2017/071399, filed Aug. 25, 2017, which claims priority to EP Application No. 16306118, filed Sep. 7, 2016, both of which are hereby incorporated herein by reference.

BACKGROUND

The invention relates to an infusion device for administering a medical fluid to a patient according to the preamble of claim 1.

An infusion device of this kind comprises a receptacle for receiving a syringe, a pusher device movable in a pushing direction for acting onto a piston of the syringe received in the receptacle, a driving rod, an electric drive device for driving the driving rod, and a clutching device for operatively connecting the driving rod to the pusher device such that a movement of the driving rod causes a movement of the pusher device for acting onto the piston of the syringe. The clutching device comprises a frame member and at least one clutch element movably arranged on the frame member, wherein the at least one clutch element is constituted to operatively connect, in a clutched state, the driving rod to the pusher device for driving the pusher device by the electric drive device. The clutching device is actuatable, for example by an actuation device such as an actuation lever, to assume an unclutched state in which the operative connection between the driving rod and the pusher device is released.

The infusion device hence is constituted as a syringe pump in which, for delivering a medical fluid—for example a medication or a nutritional fluid—from a cylindrical tube of the syringe towards a patient, a piston is moved into the cylindrical tube by means of the pusher device. During an infusion procedure the pusher device is moved, driven by the electric drive device, for example at a constant speed to deliver a medical fluid from the syringe at a desired, constant dose rate towards the patient.

The clutching device is releasable in order to allow for the installation of the syringe on the infusion device. By transferring the clutching device from the clutched state into the unclutched state, the operative connection between the driving rod and the pusher device is released, such that the pusher device can be moved independently of the driving rod and hence independently of the electric drive device. This allows to manually move the pusher device into a position in which the syringe can be placed in the receptacle of the infusion device. Upon installation of the syringe, the pusher device is approached towards the piston of the syringe and, for example by releasing an actuation lever, the clutching device is transferred back to its clutched state such that the operative connection between the driving rod and the pusher device is re-established.

Also, if a user wishes to deliver a manual bolus, the user may unclutch the clutching device, may administer the bolus and may release an actuation lever to cause clutching of the driving rod to the pusher device, such that the regular infusion procedure may resume.

In an infusion device known for example from US 2012/0215170 A1, a clutching device comprises a pair of clutch elements which are spring elastically tensioned towards the clutched state. The clutch elements herein are held in the clutched state by means of spring elements pushing the clutch elements in engagement with a threaded spindle, such that during an infusion process a rotation of the spindle is transferred into a longitudinal movement of a pusher device.

During an infusion process, the clutching device must maintain its clutched state in order to drive the pusher device in a controlled fashion. In particular, it must be avoided that forces acting onto the pusher device—for example due to a pressure rise in the syringe or an infusion line connected to the syringe—may lead to a releasing of the clutching device.

Within conventional infusion devices, to ensure that the clutching device safely maintains its clutched state, spring elements tensioning the clutch elements towards the clutched state are dimensioned to have a rather large spring stiffness, which however may have a detrimental effect on the comfort for actuating an actuation device for unclutching the clutching device.

It is an object of the instant invention to provide an infusion device which in an easy and reliable manner allows for maintaining the clutching device in the clutched state during operation of the infusion device.

SUMMARY

This object is achieved by means of an infusion device comprising the features of claim 1.

Accordingly, the clutching device comprises a lock element for locking the at least one clutch element in the clutched state.

The clutching device hence provides for a locking of the at least one clutch element in the clutched state such that the at least one clutch element is held in the clutched state in a (positive) locking fashion and not (only) by spring-elastic tensioning of one or multiple spring element. By locking the at least one clutch element, it can be achieved that even large forces, for example due to an excessive pressure rise during an infusion process, may not lead to an unclutching of the clutching device.

Because the at least one clutch element is held in the clutched state by means of the lock element, spring elements providing for the tensioning of the at least one clutch element towards the clutched state can be dimensioned with a reduced spring stiffness. During operation of the infusion device forces acting onto the pusher device and being transferred towards the clutching device are received by the lock element, such that the forces may not lead to an opening of the clutching device. Because the elastic tensioning of the at least one clutch element can be softer, the comfort for actuating the at least one clutch element for unclutching may be improved.

In one embodiment, the frame member is operatively connected to the pusher device and the at least one clutch element is constituted to releasably engage with the driving rod. The at least one clutch element may for example comprise a screw thread engaging with a corresponding screw thread of the driving rod, such that a rotational movement of the driving rod is transferred into a longitudinal movement of the frame member along the driving rod, the connection of the frame member to the pusher device causing the pusher device to be moved such that the piston of the syringe is driven by the pusher device. By releasing the at least one clutch element from the driving rod, an independent movement of the pusher device with respect to the driving rod is possible, in particular for installing a syringe on the infusion device or for performing a manual bolus.

The at least one clutch element is, in one embodiment, spring elastically tensioned towards the clutched state. The spring elastically tensioning, effected for example by means of a pressure spring, causes the at least one clutch element to move towards the clutched state as soon as an actuation device, for example in the shape of a pivotable lever for example placed on the pusher device, is released. The tensioning of the at least one clutch element causes the clutching device to regularly assume the clutched state, such that only upon actuation of the actuation device the clutching device is released and an independent movement of the pusher device from the driving rod becomes possible.

In one embodiment, the lock element is movably, for example pivotably, arranged on the at least one clutch element. The lock element hence is movable with respect to the at least one clutch element in order to lock the at least one clutch element in the clutched state and to unlock the at least one clutch element in order to transfer the clutching device from the clutched state into the unclutched state.

For actuating the clutching device, in one embodiment a cam element is provided which is operatively connected to an actuation device, for example an actuation lever. The cam element for example acts onto the at least one clutch element via a body portion which is constituted to push the at least one clutch element in a releasing direction for moving the at least one clutch element from the clutched state towards the unclutched state. The pushing movement of the at least one clutch element takes place against the spring-elastic tensioning of the at least one clutch element, the re-establishment of the clutched state then being effected by the spring-elastic tensioning upon release of the actuation device.

In one embodiment, the cam element is also constituted to act onto the lock element to move the lock element for unlocking the at least one clutch element in order to transfer the clutch device from the clutched state to the unclutched state. The movement of the at least one clutch element and the movement of the lock element hence are caused by the (same) cam element, which unlocks the lock element and, possibly with a slight delay, causes the at least one clutch element to move such that the engagement of the clutch element with the driving rod is released. Because no separate actuation mechanism (besides the cam element) is required for actuating the lock element, the system may be implemented in an easy way and may provide for a reliable operation.

In one embodiment, a spring element acts onto the lock element to lock the at least one clutch element in the clutched state. Said spring element tensions the lock element towards a locked position in which the lock element locks the at least one clutch element in the clutched state. Hence, upon moving the at least one clutch element into the clutched state, the lock element automatically assumes its locked position such that the at least one clutch element is locked.

In one embodiment, the spring element tensioning the lock element towards its locked position also causes a tensioning of the at least one clutch element towards the clutched state. The tensioning of the lock element and the tensioning of the at least one clutch element hence are provided by the same spring element, which may further ease the mechanics of the system and the number of required parts.

In one embodiment, the clutching device comprises two clutch elements, each clutch elements being movably arranged on the frame member, wherein the two clutch elements are movable (in particular pivotable) in opposite directions for transferring the clutching device into the unclutched state. The lock element herein beneficially locks the two clutch elements with respect to each other in the clutched state such that the two clutch elements cannot be moved apart from one another without unlocking the lock element. The clutch elements hence are secured in the clutched state, and the operative connection between the driving rod and the pusher device is reliably held a means of the lock element.

In one embodiment, the lock element is pivotably arranged on a first of the two clutch elements and comprises a lock arm for engaging with a second of the two clutch elements for locking the clutch elements with respect to each other. The lock element hence acts as a locking pawl which is pivotably connected to one of the clutch elements and engages with the other clutch element in a positive locking fashion such that no relative movement of the clutch elements with respect to each other is possible if the lock element is locked. Only upon pivoting the lock element, beneficially caused by a cam element also serving to push the clutch elements apart from one another, the clutch elements can be moved to disengage from the driving rod.

BRIEF DESCRIPTION OF THE DRAWINGS

The idea underlying the invention shall subsequently be described in more detail with respect to the embodiments shown in the figures. Herein:

FIG. 2 shows a schematic view of a drive mechanism of the infusion device;

FIG. 3 shows a schematic view of a clutching device of a drive element of the drive mechanism;

FIG. 8A shows another embodiment of a clutching device, in a clutched state;

FIG. 8B shows the clutching device during unclutching;

FIG. 8C shows the clutching device in an unclutched state;

FIG. 9A shows another embodiment of a clutching device in a clutched state;

FIG. 9B shows the clutching device during unclutching; and

FIG. 9C shows the clutching device in an unclutched state.

DESCRIPTION OF THE EMBODIMENTS

Figure 1:
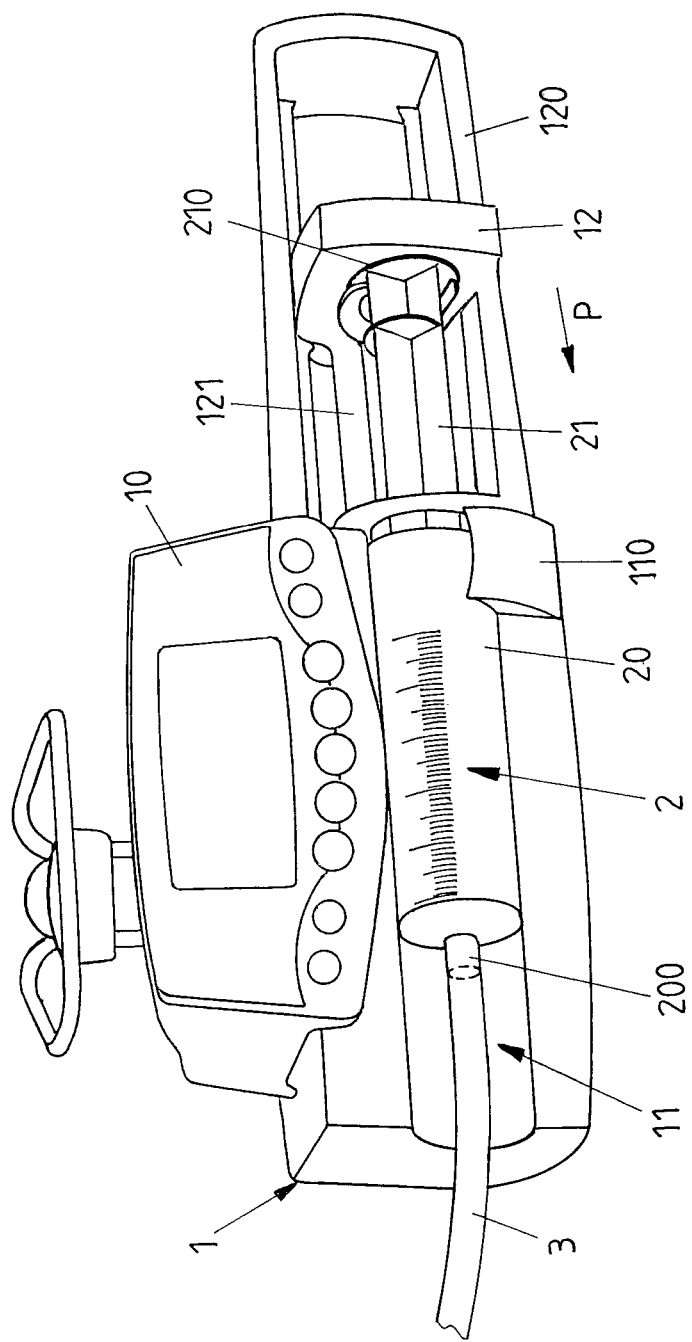
FIG. 1 shows a view of an embodiment of an infusion device in the shape of a syringe pump.
Figure 4:
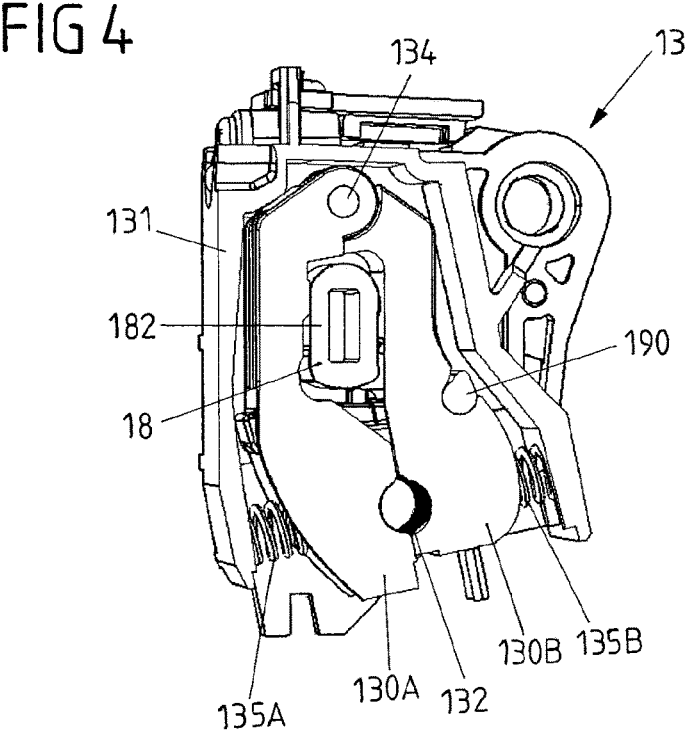
FIG. 4 shows a view of an embodiment of a clutching device comprising two clutch elements.

FIG. 1 shows an infusion device 1 in the shape of a syringe pump having a housing 10 and a receptacle 11 arranged on the housing 10 to receive a syringe 2 therein.

The syringe 2 comprises a cylindrical tube 20 which, when installing the syringe 2 on the infusion device 1, contains a medical liquid, for example a medication or a solution for the parenteral feeding, to be infused to a patient. The cylindrical tube 20 is connected, via a connector 200, to an infusion line 3 which may extend from the syringe 2 towards a patient for infusing the medical liquid to the patient.

For installing the syringe 2 on the receptacle 11 of the infusion device 1, the cylindrical tube 20 of the syringe 2 is placed in the receptacle 11 and is mechanically connected to the housing 10 by means of a fixation device 110. By means of the fixation device 110, for example constituted by a releasable clamp element, the cylindrical tube 20 is secured within the receptacle 11 such that the cylindrical tube 20 is held in position on the receptacle 11.

The syringe 2 comprises a piston 21 which, for delivering medical fluid contained in the cylindrical tube 20, can be pushed into the cylindrical tube 20 in a pushing direction P. For this, the infusion device 1 comprises a pusher device 12 movably arranged within a guide device 120 and connected to a drive mechanism (which subsequently shall be described with relation to FIGS. 2 and 3) via a connecting rod 121.

For operating the infusion device 1, the syringe 2 is installed on the infusion device 1 and the pusher device 12 is (manually) moved towards a piston head 210 of the piston 21 until the pusher device 12 comes into abutment with the piston head 210. For performing an infusion process the pusher device 12 is then electrically moved in the pushing direction P to move the piston 21 into the cylindrical tube 20 for delivering the medical fluid contained in the cylindrical tube 20 via the infusion line 3 towards the patient.

The pusher device 12 is driven by a drive mechanism, which, according to one embodiment, is schematically illustrated in FIG. 2. The drive mechanism comprises a drive element 13, which is connected to the pusher device 12 via the connecting rod 121 in a mechanically fixed manner such that by moving the drive element 13 the pusher device 12 is moved along the pushing direction P. The drive element 13 is movable within the housing 10 along the pushing direction P and, via a clutching device 130, is (releasably) connected to a driving rod 14 having a screw thread 140.

A schematic, simplified drawing of a clutching device 130 is shown in FIG. 3. The clutching device comprises two clutch elements 130 which each are pivotably connected, about an associated pivot axis 134, to a frame member 131 of the drive element 13. The clutch elements 130 each are shaped as a half nut and comprise a rod receptacle in the shape of screw thread 132 by which they may engage with the screw thread 140 of the driving rod 14.

In a clutched state, as illustrated in FIG. 3, the clutch elements 130 are pivoted towards each other in a clutching direction C such that they receive the driving rod 14 in between them and engage with the screw thread 140 of the driving rod 14. To release the engagement, the clutch elements 130 are pivoted opposite to the clutching direction C away from one another, such that they disengage from the screw thread 140 of the driving rod 14 and hence release the connection between the drive element 13 and the driving rod 14.

During regular infusion operation of the infusion device 1 the clutch device is in the clutched state in which the clutch elements 130 engage with the screw thread 140 of the driving rod 14. The driving rod 14, at one end, is connected to an electric drive motor 141 and at the other end is received in a bearing 142 such that, driven by the electric drive motor 141, the driving rod 14 can be rotated about an axis of rotation R1. By rotating the driving rod 14, the drive element 13 (due to the engagement of the clutch elements 130 with the screw thread 140 of the driving rod 14) is longitudinally moved along the driving rod 14, and by the movement of the drive element 13 the pusher device 12 pushes the piston 21 in the pushing direction P into the cylindrical tube 20 of the syringe 2.

The drive element 13 is operatively connected to a brake device 16 having a threaded spindle 160 which is rotatable, within bearings 161, about a rotational axis R2. The drive element 13 comprises an engagement opening 133 having a screw thread therein which engages with a screw thread of the threaded spindle 160. A longitudinal movement of the drive element 13 along the pushing direction P hence causes, due to the engagement, the threaded spindle 160 to be rotated about the rotational axis R2, which generally may be possible at low force if the screw thread of the threaded spindle 160 has a comparatively large pitch.

The threaded spindle 160, at one end, is associated with a brake 162 constituted for example by an electromagnetic brake. If the brake 162 is activated, it blocks a rotation of the threaded spindle 160 about its rotational axis R2. If the threaded spindle 160 is not able to rotate, the drive element 13 cannot move along the threaded spindle 160 such that the drive element 13 is held in position and hence is braked by the brake device 16. If the brake 162 in contrast is deactivated, the threaded spindle 160 is allowed to rotate, such that the drive element 13 is not braked and may be moved longitudinally along the threaded spindle 160.

The operation of the infusion device 1 is controlled by means of a control device 17. In particular, the control device 17 acts onto the electric drive device 141 to rotate the driving rod 14, and the control device 17 acts onto the brake 162 to switch the brake device 16 between its activated and its deactivated state.

The clutch device implemented by the clutch elements 130 is actuatable by means of an actuation device 15, for example in the shape of a lever for example arranged on the pusher device 12. Herein, the lever may be manually pressed to unclutch the clutch elements 130 from the driving rod 14, and may be released in order to revert the clutching device 13 to its clutched state.

The drive mechanism as schematically illustrated in FIGS. 2 and 3 may, in one embodiment, be implemented by a mechanism as it is described in US 2012/0215170 A1, which shall be incorporated by reference herein.

In addition, sensing devices 170, 171 are provided which serve to monitor an actuation state of the actuation device 15 and a force between the pusher device 12 and the piston head 210 of the piston 21.

As said, for installing a syringe 2 on the infusion device 1 the pusher device 12 is manually moved such that it comes into contact with the piston 21. For this, the clutching device is actuated by means of the actuation device 15 to its unclutched state, such that the drive element 13 can freely be moved along the driving rod 14. Once the pusher device 12 has come into contact with the piston head 210 of the piston 21, the clutching device is manually brought into engagement with the driving rod 14 by releasing the lever of the actuation device 15.

In addition, during operation of the infusion device it is conceivable that a user may want to perform a manual bolus by manually pushing the pusher device 12 in the pushing direction P to push the piston 21 into the cylindrical tube 20. For this, the clutching device is unclutched such that the pusher device 12 is manually movable, and, after the manual bolus has been performed, is reverted to its clutched state such that the regular infusion operation may resume.

FIGS. 4 to 7A-7C show a first, specific embodiment of a clutching device 13 having a frame member 131 to which two clutch elements 130A, 130B are pivotably connected via a common pivot axis 134. Each clutch element 130A, 130B comprises a rod receptacle 132 in the shape of a screw thread such that, in a clutched state of the clutching device 13, the driving rod 14 is received in between the clutch elements 130A, 130B and the rod receptacle 132 of each clutch element 130A, 130B engages with the screw thread 140 of the driving rod 14. As described above, a rotational movement of the driving rod 14 hence causes a longitudinal movement of the frame member 131 along the driving rod 14, the connecting rod 121 being fixedly connected to the frame member 131 such that the pusher device 12 is moved along with the frame member 131.

Each clutch element 130A, 130B is elastically tensioned with respect to the frame member 131 by means of a spring element 135A, 135B in the shape of a push spring. The tensioning herein acts towards the clutched state such that the clutch elements 130A, 130B are pushed towards each other for engaging with the driving rod 14 placed in between the clutch elements 130A, 130B.

Figure 5:
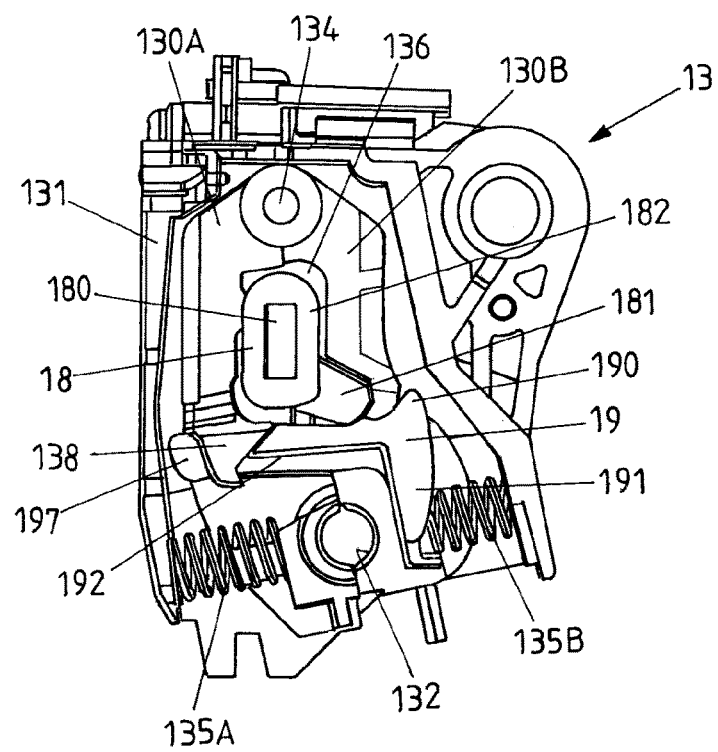
FIG. 5 shows a sectional view of the clutching device.

As visible from FIG. 5, a lock element 19 is pivotably arranged, via a pivot axis 190, on a first clutch element 130B of the two clutch elements 130A, 130B. The lock element 19 comprises a lock arm 192 reaching from the pivot axis 190 towards the other, second clutch element 130A and having a locking contour 197 engaging, in the clutched state of the clutching device 13, with a locking protrusion 138 of the other, second clutch element 130A, as shown in FIG. 5.

Via the lock element 19 the clutch elements 130A, 130B hence are locked with respect to each other in the clutched state of the clutching device 13, such that forces acting onto the clutching device 13—due to for example a pressure rise in the syringe 2 or in the infusion line 3 connected to the syringe 2—may not lead to an opening of the clutching device 13.

The lock element 19 comprises, at approximately a perpendicular angle with respect to the lock arm 192, a tensioning arm 191 which is in abutment with the spring element 135B associated with the first clutch element 130B. By acting onto the tensioning arm 191 the spring element 135B indirectly acts onto the first clutch element 130B towards the clutched state, wherein the spring element 135B tensions the lock element 19 towards a locking position in which the lock element 19 with the lock arm 192 is in locking engagement with the locking protrusion 138 of the other, second clutch element 130A. When the clutching device 13 is in the clutched state, thus, the lock element 19 automatically is moved to its locked position such that the clutch elements 130A, 130B are locked with respect to each other and cannot be moved apart from one another without unlocking the lock element 19.

The unclutching of the clutching device 13 takes place via a cam element 18 having a body portion 182 received in an inner space 136 in between the clutch elements 130A, 130B. The cam element 18 is in connection with a shaft 180 being in operative connection with the actuation device 15 and being pivoted upon actuation of the actuation device 15, as it can be seen for example in the sequence of FIG. 7A to 7C.

Figure 6:
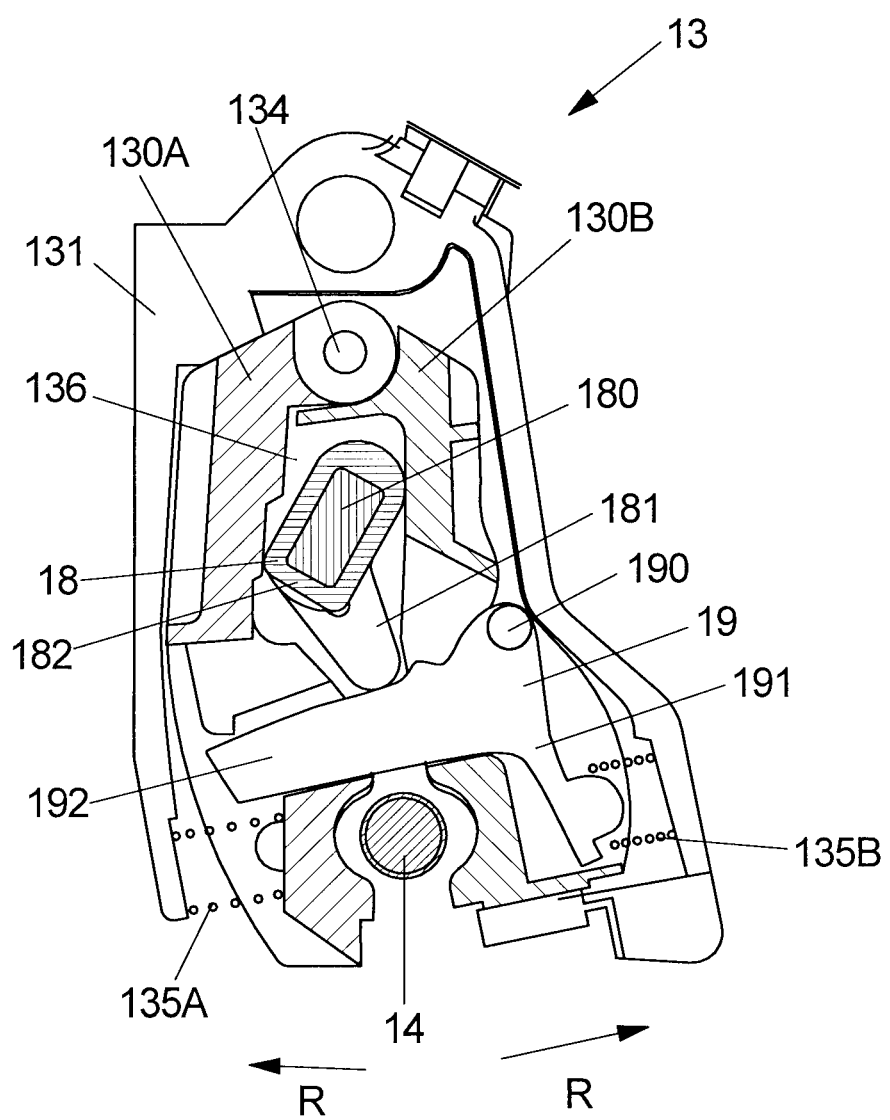
FIG. 6 shows a sectional view of the clutching device, in an unclutched state.
Figure 7A:
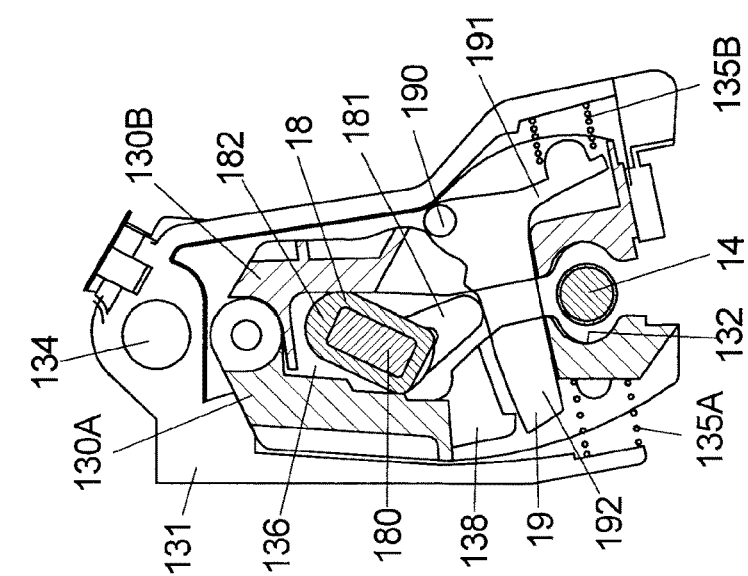
FIG. 7A shows the clutching device in a clutched state.
Figure 7B:
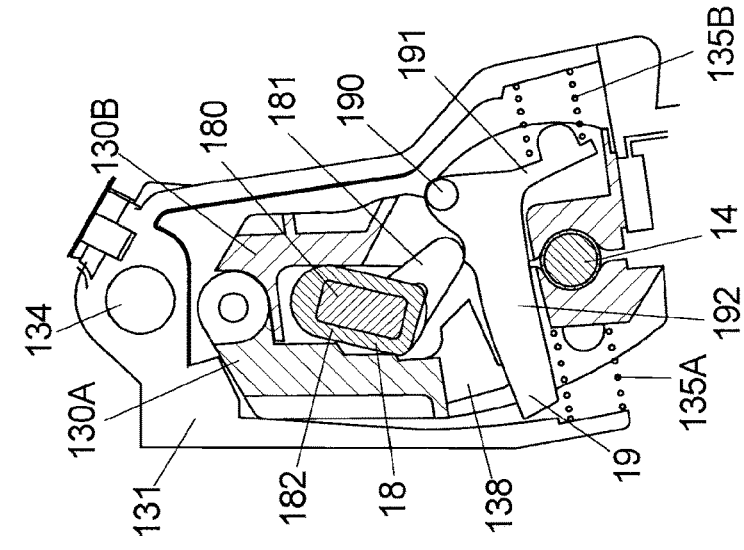
FIG. 7B shows the clutching device during unclutching.
Figure 7C:
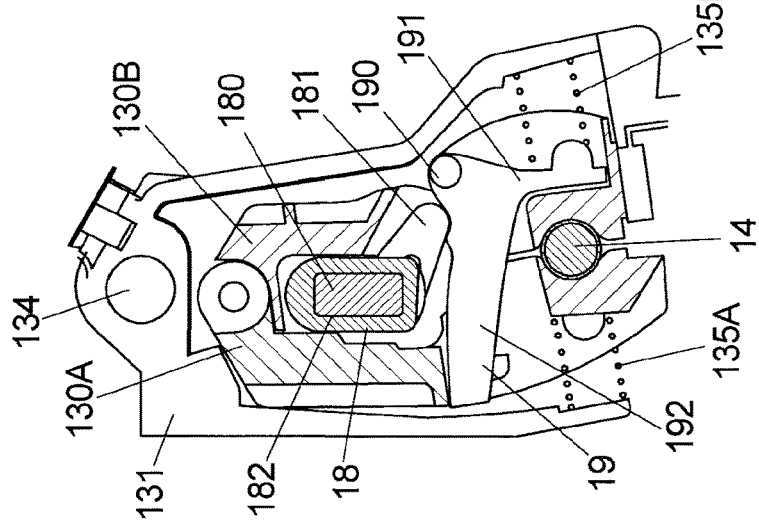
FIG. 7C shows the clutching device in the unclutched state.

The cam element 18 serves to push apart the clutch elements 130A, 130B in a releasing direction R, as it can be seen from FIG. 6 and from FIG. 7C. By moving the body portion 182, the clutch elements 130A, 130B are pushed apart against the tensioning forces of the spring elements 135A, 135B, such that the engagement of the rod receptacles 132 of the clutch elements 130A, 130B with the driving rod 14 is released, as shown in FIG. 7C.

The cam element 18, when actuated to unclutch the clutching device 13, also acts onto the lock element 19. For this, the cam element 18 comprises a lever arm 181 protruding from the body portion 182 and being in abutment with the lock arm 192 of the lock element 19. When the cam element 18 is pivoted for unclutching the clutching device 13, the lever arm 181 acts onto the lock arm 192 of the lock element 19 and pushes the lock arm 192 downwards such that the engagement of the locking contour 197 with the locking protrusion 138 is released, as it can be seen in FIG. 7B. The unlocking of the lock element 19 takes place slightly ahead of the pushing apart of the clutch elements 130A, 130B, such that the lock element 19 is first unlocked before the clutch elements 130A, 130B are substantially pushed apart for releasing the engagement with the driving rod 14, as shown in FIG. 7C.

Because the locking of the clutch elements 130A, 130B in the clutched state of the clutching device 13 is achieved by the lock element 19, the forces acting onto the clutch elements 130A, 130B during an infusion process (for example due to a pressure rise in the infusion set) are received by the lock element 19. This allows to dimension the spring elements 135A, 135B to have a rather low spring stiffness, such that the spring elements 135A, 135B may be rather soft, allowing for an easy, comfortable unclutching of the clutching device 13, because rather low forces are required to push the clutch elements 130A, 130B apart in the releasing direction R against the tensioning forces of the spring elements 135A, 135B.

In another embodiment shown in FIGS. 8A to 8C clutch elements 130A, 130B are pivotably arranged on a frame member 131 about a common pivot axis 134, each clutch element 130A, 130B being tensioned with respect to the frame member 131 by means of a spring element 135A, 135B. In this embodiment, the lock element 19 is pivotably arranged about a pivot axis 190 on the clutch element 130A and, in the clutched state of the clutching device 13, engages via a locking receptacle 194 with a lock pin 137 of the other clutch element 130B. The lock element 19 herein is tensioned with respect to the other clutch element 130B by means of a spring element 193 in the shape of a pull spring, such that the lock element 19 is automatically locked when the clutching device 13 assumes its clutched state.

The actuation of the clutching device 13 for transferring the clutching device 13 into the unclutched state is substantially the same as for the embodiment described above. A cam element 18 is pivoted by rotating a shaft 180, such that a body portion 182 pushes the clutch elements 130A, 130B apart from one another and the engagement of the clutch elements 130A, 130B with the driving rod 14 is released, as it is shown in FIG. 8C. Slightly ahead of the movement of the clutch elements 130A, 130B, a lever arm 181 protruding from the body portion 182 acts onto the lock element 19 such that the lock element 19 is released from its engagement with the lock pin 137, as it can be seen in FIG. 8B. Upon releasing the locking engagement, the clutch elements 130A, 130B can be pushed apart for releasing the engagement with the driving rod 14, as shown in FIG. 8C.

In another embodiment shown in FIG. 9A to 9C, two clutch elements 130A, 130B are pivotably arranged on a frame member 131 about a common pivot axis 134. As in the embodiment of FIG. 8A to 8C, each clutch element 130A, 130B is tensioned with respect to the frame member 131 by means of a spring element 135A, 135B towards the clutched state.

In this embodiment, the lock element 19 is slideably arranged within the frame member 131 by engagement of longitudinal holes with the pivot axis 134 and shaft 180. The lock element 19 comprises, at its foot, a locking section 196 which, in the clutched state of the clutching device 13, engages and reaches around a locking protrusion 139 formed by the clutch elements 130A, 130B in the area of the rod receptacles 132, as it can be seen in FIG. 9A. Via the locking section 196, hence, the clutch elements 130A, 130B are locked with respect to each other in the clutched state.

The cam element 18, via the lever arm 181, acts onto a pin 195 of lock element 19 such that the lock element 19 is slid upwards when actuating the cam element 18 for unclutching the clutching device 13 and the engagement of the locking section 196 with the locking protrusion 139 is released, as can be seen in FIGS. 9B and 9C. The releasing of the locking, as shown in FIG. 9B, herein takes place before the clutch elements 130A, 130B are substantially moved apart from one another. Only upon releasing the locking the clutch elements 130A, 130B are moved to release the engagement of the clutch elements 130A, 130B with the driving rod 14, as it is shown in FIG. 9C.

The idea underlying the invention is not limited to the embodiments described above, but may be implemented in an entirely different fashion in entirely different embodiments.

An infusion device of the kind described herein may serve different purposes and may in particular be used to deliver a medical fluid such as a medication or a nutritional fluid, for example for the enteral or parenteral feeding, towards a patient.

In principle, a clutching device may also comprise only a single clutch element. In this case, the lock element may serve to lock the single clutch element when the clutching device is in the clutched state.

LIST OF REFERENCE NUMERALS

1 Infusion device
10 Housing
11 Receptacle
110 Fixation device
12 Pusher device
120 Guide device
121 Connecting rod
13 Drive element
130, 130A, 130B Clutch element
131 Frame member
132 Rod receptacle
133 Engagement opening
134 Pivot axis
135A, 135B Spring element
136 Inner space
137 Lock pin
138 Locking protrusion
139 Locking protrusion
14 Driving rod (spindle)
140 Screw thread
141 Drive motor
142 Bearing
15 Actuation device (handle)
16 Brake device
160 Threaded spindle
161 Bearing
162 Brake
17 Control device
170, 171 Sensing device
18 Cam element
180 Shaft
181 Lever arm
182 Body portion
19 Lock element
190 Pivot axis
191 Tensioning arm
192 Lock arm
193 Spring element
194 Locking receptacle
195 Pin
196 Locking section
197 Locking contour
2 Syringe
20 Cylinder tube
200 Connector
21 Piston
210 Piston head
3 Infusion line
C Clutching direction
P Pushing direction
R Releasing direction
R1, R2 Axis of rotation

The invention claimed is:

1. An infusion device for administering a medical fluid to a patient, comprising:
a receptacle for receiving a syringe,
a pusher device movable in a pushing direction for acting onto a piston of the syringe received in the receptacle,
a driving rod,
an electric drive device for driving the driving rod, and
a clutching device comprising a frame member and at least one clutch element movably arranged on the frame member, the at least one clutch element being configured to operatively connect, in a clutched state, the driving rod to the pusher device for driving the pusher device by the electric drive device, the clutching device being actuatable to assume an unclutched state in which the operative connection between the driving rod and the pusher device is released,
wherein the clutching device comprises a lock element for locking the at least one clutch element in the clutched state,
wherein the clutching device comprises two clutch elements, each clutch element being movably arranged on the frame member, wherein the two clutch elements are movable in opposite directions for transferring the clutching device into the unclutched state, and
wherein the lock element is pivotably arranged on a first of the two clutch elements and comprises a lock arm for engaging with a second of the two clutch elements for locking the clutch elements with respect to each other.

2. The infusion device according to claim 1, wherein the frame member is operatively connected to the pusher device and the at least one clutch element is configured to releasably engage with the driving rod.

3. The infusion device according to claim 1, wherein the at least one clutch element is spring elastically tensioned towards the clutched state.

4. The infusion device according to claim 1, further comprising a cam element operatively connected to an actuation device for moving the at least one clutch element to transfer the clutch device between the clutched state and the unclutched state.

5. The infusion device according to claim 4, wherein the cam element comprises a body portion configured to push the at least one clutch element in a releasing direction for moving the at least one clutch element from the clutched state towards the unclutched state.

6. The infusion device according to claim 4, wherein the cam element is configured to act onto the lock element to move the lock element for unlocking the at least one clutch element when transferring the clutch device from the clutched state to the unclutched state.

7. The infusion device according to claim 1, further comprising a spring element acting onto the lock element to lock the at least one clutch element in the clutched state.

8. The infusion device according to claim 7, wherein said spring element is configured to tension the at least one clutch element towards the clutched state.

9. The infusion device according to claim 1, wherein the lock element locks the two clutch elements with respect to each other in the clutched state.

10. The infusion device according to claim 1, wherein each clutch element comprises a rod receptacle for receiving the driving rod between the clutch elements to engage with the driving rod for operatively connecting the driving rod to the pusher device.

* * * * *